US006682750B2

United States Patent
Löffler et al.

(10) Patent No.: US 6,682,750 B2
(45) Date of Patent: Jan. 27, 2004

(54) SURFACTANT-FREE COSMETIC, DERMATOLOGICAL AND PHARMACEUTICAL COMPOSITIONS

(75) Inventors: Matthias Löffler, Niedernhausen (DE); Roman Morschhäuser, Mainz (DE); Michael Hornung, Frankfurt (DE)

(73) Assignee: Clariant GmbH, Frankfurt (DE)

( * ) Notice: Subject to any disclaimer, the term of this patent is extended or adjusted under 35 U.S.C. 154(b) by 120 days.

(21) Appl. No.: 10/086,039

(22) Filed: Feb. 28, 2002

(65) Prior Publication Data

US 2002/0176835 A1 Nov. 28, 2002

(30) Foreign Application Priority Data

Mar. 3, 2001 (DE) .......................................... 101 10 336

(51) Int. Cl.[7] .............................. A61K 6/00; A61K 7/00; A61K 31/16; C08F 226/06
(52) U.S. Cl. ........................ 424/401; 526/264; 514/613
(58) Field of Search ..................... 526/264; 424/401; 514/613

(56) References Cited

U.S. PATENT DOCUMENTS

| | | | |
|---|---|---|---|
| 4,619,773 A | * | 10/1986 | Heilweil et al. |
| 5,510,436 A | * | 4/1996 | Hille et al. |
| 5,736,125 A | | 4/1998 | Morawsky et al. |
| 5,756,077 A | * | 5/1998 | Syed et al. |
| 5,833,951 A | | 11/1998 | Artz et al. |
| 6,054,138 A | | 4/2000 | Trebosc et al. |
| 6,355,752 B1 | | 3/2002 | Brungs et al. |

FOREIGN PATENT DOCUMENTS

| | | |
|---|---|---|
| DE | 44 25 268 | 1/1996 |
| WO | 96/37180 | 11/1996 |

* cited by examiner

Primary Examiner—Sreeni Padmanabhan
Assistant Examiner—S. Jiang
(74) Attorney, Agent, or Firm—Richard P. Silverman

(57) ABSTRACT

The invention relates to surfactant-free cosmetic, dermatological and pharmaceutical compositions, comprising at least one copolymer consisting essentially of a1) 1 to 50% by weight of the repeat structural unit of the formula (1)

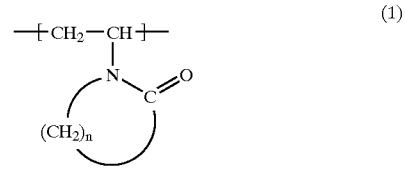

where n is an integer from 2 to 9, or a2) 1 to 50% by weight of a mixture of the repeat structural unit of the formula (1) and the repeat structural unit of the formula (2)

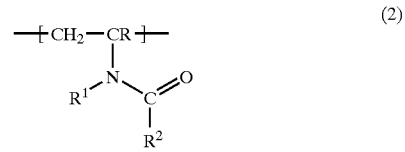

where R, $R^1$ and $R^2$ may be identical or different and are hydrogen or a linear or branched alkyl or alkenyl group having in each case 1 to 30 carbon atoms and b) 49.99 to 98.99% by weight of the repeat structural unit of the formula (3)

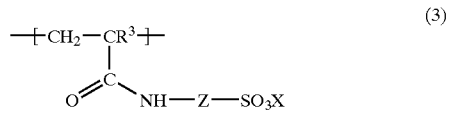

in which $R^3$ is hydrogen, methyl or ethyl, Z is ($C_1$–$C_8$)-alkylene, n is an integer from 2 to 9 and X is an ammonium, alkali metal or alkaline earth metal ion and c) 0.01 to 8% by weight of crosslinking structures which originate from monomers having at least two olefinic double bonds.

20 Claims, No Drawings

SURFACTANT-FREE COSMETIC, DERMATOLOGICAL AND PHARMACEUTICAL COMPOSITIONS

The present invention relates to surfactant-free cosmetic, pharmaceutical and dermatological compositions comprising crosslinked water-soluble or water-swellable copolymers based on acrylamidoalkylsulfonic acids and cyclic N-vinylcarboxamides and/or linear N-vinylcarboxamides.

Cosmetic skincare compositions primarily have the task of strengthening or restoring the natural function of the skin as a barrier against environmental influences (e.g. dirt, chemicals, microorganisms) and against the loss of endogenous substances (e.g. water, natural fats, electrolytes).

Another aim of skincare is to compensate for the loss of sebum and water from the skin caused by daily washing.

Medicinal formulations for the skin generally comprise one or more medicaments in an effective concentration.

The cosmetic or dermatological compositions currently used are mostly in the form of oil-in-water emulsions or water-in-oil emulsions.

Water-in-oil emulsions comprise a continuous oil phase and permit a fatty film to form on the surface of the skin which prevents transepidermal water loss and protects the skin against external aggressions.

Such emulsions are particularly suitable for protecting the skin and for the treatment of dry skin.

By contrast, oil-in-water emulsions impart to the skin upon application a soft, less greasy and pleasant feel.

The emulsions are generally stabilized by incorporating emulsifying surfactants of the oil-in-water (ONV) type or of the water-in-oil (W/O) type.

In order to achieve adequate stability of the emulsions, such surfactants must, however, in most cases be added in amounts up to 10% by weight, based on the total weight of the emulsions. Emulsions without surfactants generally exhibit inadequate stabilization of the oil components, which leads to coagulation and separation of the oil phases.

A disadvantage of using surfactants is that they can lead to irritation of the skin, the eyes and the scalp or, in individual cases, may even trigger an allergic reaction. Thus, for example, it is known that certain surfactants can trigger photodermatoses upon simultaneous exposure to sunlight. A further disadvantage is that high surfactant concentrations can lead to a rough, sticky or viscous feel of the compositions or make the compositions appear compact and heavy. Moreover, the surfactants have to be chosen depending on the polarity of the oils, meaning that the variety of formulations is limited.

The users of emulsions have therefore continually made efforts to reduce the surfactant content in order to improve the compatibility of the emulsions and to optimize their cosmetic properties.

Over the course of recent years, polymers which permit the formulation of low-surfactant and even surfactant-free emulsions have become established on the market (WO 96/37180 and U.S. Pat. No. 5,736,125). These polymers are hydrophobic modifications of conventional poly(meth)acrylates which have both thickening and also emulsifying/dispersing properties. Examples of commercial products are ®Pemulen TR-1 and TR-2 from BF-Goodrich and ®Aculyn 22 and ®Aculyn 28 from Rohm und Haas.

Since polymers hydrophobically modified in this way are constructed on the basis of (meth)acrylic acid, they subsequently have the disadvantages of poly(meth)acrylates. A significant disadvantage of thickeners based on poly(meth)acrylic acid is the considerable pH dependency of the thickening ability. Thus, an adequate viscosity is generally only brought about if the pH of the formulation is adjusted above pH 6.0 and thus the poly(meth)acrylic acid is present in neutralized form.

DE 44 25 268 describes emulsifier-free, finely disperse oil-in-water preparations which comprise acrylic acid polymers as thickeners, but which are likewise unsuitable for acidic formulations.

Surprisingly, it has now been found that crosslinked copolymers based on acrylamidoalkylsulfonic acid and cyclic N-vinylcarboxamides and/or cyclic N-vinylcarboxamides are highly suitable as thickener, stabilizer, dispersant and lubricant in surfactant-free cosmetic, dermatological and pharmaceutical compositions.

Advantageously, the copolymers exhibit very good thickening properties over a wide pH range, i.e. even at an acidic pH.

The invention thus provides surfactant-free cosmetic, dermatological and pharmaceutical compositions, comprising at least one copolymer consisting essentially of a1) 1 to 50% by weight of the repeat structural unit of the formula (1)

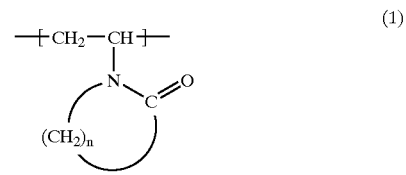

where n is an integer from 2 to 9, or a2) 1 to 50% by weight of a mixture of the repeat structural unit of the formula (1) and the repeat structural unit of the formula (2)

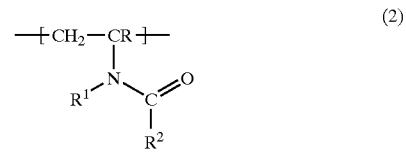

where R, $R^1$ and $R^2$ may be identical or different and are hydrogen or a linear or branched alkyl or alkenyl group having in each case 1 to 30, preferably 1 to 20, in particular 1 to 12, carbon atoms and b) 49.99 to 98.99% by weight of the repeat structural unit of the formula (3)

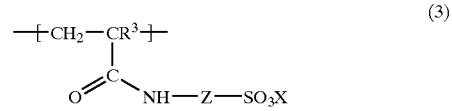

in which $R^3$ is hydrogen, methyl or ethyl, Z is $(C_1-C_8)$-alkylene, n is an integer from 2 to 9 and X is an ammonium, alkali metal or alkaline earth metal ion and c) 0.01 to 8% by weight of crosslinking structures which originate from monomers having at least two olefinic double bonds.

The mixing ratio with regard to structural unit a2) can vary within any desired limits.

Preferred copolymers comprise 2 to 30% by weight, particularly preferably 3 to 15% by weight, of the structural units a1) or a2), preferably of the structural unit a2), 69.5 to 97.5% by weight, particularly preferably 84.5 to 96.5% by weight, of the structural unit b) and 0.01 to 5% by weight, particularly preferably 0.2 to 3% by weight, especially preferably 0.5 to 2% by weight, of the structural unit c).

Particularly preferred structural units according to formula (1) are derived from N-vinylpyrrolidone.

Suitable structural units according to formula (3) are preferably ammonium salts of 2-acrylamido-2-methylpropanesulfonic acid, particularly preferably the $NH_4^+$ salt.

The crosslinking structural units c) are preferably derived from allyl acrylate or allyl methacrylate, trimethylolpropane triacrylate, trimethylolpropane trimethacrylate dipropylene glycol diallyl ether, polyglycol diallyl ether, triethylene glycol divinyl ether, hydroquinone diallyl ether, tetraallyloxyethane or other allyl or vinyl ethers of multifunctional alcohols, tetraethylene glycol diacrylate, triallylamine, trimethylolpropane diallyl ether, methylenebisacrylamide and/or divinylbenzene. Particular preference is given to allyl acrylate, allyl methacrylate, trimethylolpropane triacrylate and/or trimethylolpropane trimethacrylate.

The crosslinking structures are especially preferably derived from monomers of the formula (4)

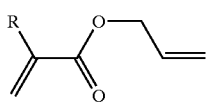

(4)

in which R is hydrogen, methyl or ethyl.

The copolymers are preferably water-soluble or water-swellable copolymers.

The copolymers are preferably prepared by free-radical copolymerization, preferably by precipitation polymerization, particularly preferably in tert-butanol. Preferably, the monomers corresponding to the formulae (1), (2) and (3) are dissolved or dispersed in a protic solvent, then one or more crosslinkers c) are added to this solution or dispersion, and polymerization is started in a known manner by adding a free-radical-forming compound.

The polymerization reaction is preferably carried out in a water-soluble alcohol or a mixture of two or more alcohols having 1 to 6 carbon atoms, preferably in tert-butanol. The water content of the alcohol or alcohol mixture should not exceed 10% by weight since otherwise clumping can arise in the course of the polymerization. The type and amount of solvent should be chosen so that the salt of the acrylamidoalkylsulfonic acid corresponding to formula (3), in particular of 2-acrylamido-2-methylpropanesulfonic acid, is largely soluble or dispersible therein. Largely soluble or dispersible is to be understood as meaning that no solid material settles out of the solution or dispersion when the stirrer is switched off. The polymer which forms in the course of the reaction should, by contrast, be largely insoluble in the chosen solvent or solvent mixture. Largely insoluble is to be understood here as meaning that, in the course of the polymerization, a readily stirrable, pulpy polymer paste forms in which no clumps or agglutinations form. The filtrate obtainable by filtering the paste with suction should have a solids content of at most 5% by weight. If the copolymers are soluble in the chosen solvent or solvent mixture to a greater extent, agglutinations may arise during drying of the polymer paste.

The polymerization reaction itself is started in a manner known per se by free-radical-forming compounds such as azo initiators (e.g. azobisisobutyronitrile), peroxides (e.g. dilauryl peroxide) or persulfates in the temperature interval from 20 to 120° C., preferably between 40 and 80° C., and is continued over a period of from 30 minutes to a few hours.

The property profile of the copolymers can be varied by varying the above mixing ratio of the monomers and of the crosslinkers. Thus, for example, the increased incorporation of ammonium salts of acrylamidosulfonic acids can improve the thickening action of the polymers. By contrast, incorporating more cyclic N-vinylcarboxamide improves the electrolyte compatibility of the polymers and the solubility thereof in nonaqueous systems.

Particular preference is given to copolymerizing $NH_4^+$ salts as acrylamidopropylsulfonic acid salts. In place of the ammonium salts, it is also possible to use the free acrylamidopropylsulfonic acids and, prior to the addition of the remaining monomers, to generate the ammonium salts by introducing ammonia.

The compositions according to the invention preferably comprise 0.01 to 10% by weight, particularly preferably 0.1 to 5% by weight, especially preferably 0.5 to 3% by weight, of copolymers.

The compositions can further comprise oily substances, organic solvents, cationic polymers, silicone compounds, film formers, superfatting agents, moisturizing agents, stabilizers, biogenic active ingredients, glycerol, preservatives, pearlizing agents, dyes and fragrances, solvents, hydrotropic agents, opacifiers, thickeners, dispersants, protein derivatives, such as e.g. gelatine, collagen hydrolysates, natural or synthetic-based polypeptides, egg yolk, lecithin, lanolin and lanolin derivatives, deodorizing agents, substances with a keratolytic and keratoplastic action, enzymes, carrier substances, antioxidants, UV light protection filters, pigments and metal oxides, agents with an antimicrobial action and/or acidic active ingredients.

Suitable oily substances are, preferably, silicone oils (volatile, nonvolatile, linear, branched, cyclic, optionally organically modified), phenylsilicones, silicone resins and gums, mineral oils (e.g. paraffin oil or Vaseline oil), animal oils (e.g. perhydrosqualene, lanolin), vegetable oils (liquid triglycerides, e.g. sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's smock oil, castor oil, triglycerides of caprylic/capric acids, olive oil, peanut oil, rapeseed oil and coconut oil), synthetic oils (e.g. purcellin oil, isoparaffins), linear and/or branched fatty alcohols and fatty acid esters (preferably Guerbet alcohols having 6 to 18, preferably 8 to 10, carbon atoms), esters of linear ($C_6$–$C_{13}$)-fatty acids with linear ($C_6$–$C_{20}$)-fatty alcohols, esters of branched ($C_6$–$C_{13}$)-carboxylic acids with linear ($C_6$–$C_{20}$)-fatty alcohols, esters of linear ($C_6$–$C_{18}$)-fatty acids with branched alcohols (preferably 2-ethylhexanol), esters of linear and/or branched fatty acids with polyhydric alcohols (e.g. dimerdiol or trimerdiol) and/or Guerbet alcohols, triglycerides based on ($C_6$–$C_{10}$)-fatty acids, esters (e.g. dioctyl adipates, diisopropyl dimer dilinoleates, propylene glycols/dicaprylates), waxes (e.g. beeswax, paraffin wax or microcrystalline waxes) optionally in combination with hydrophilic waxes (e.g. cetylstearyl alcohol), fluorinated and perfluorinated oils; fluorinated silicone oils and mixtures of said compounds.

The oil proportion of the compositions can, based on the finished compositions, be up to 95% by weight, preferably 2 to 95% by weight, particularly preferably 2 to 50% by weight, especially preferably 5 to 20% by weight.

The proportion of oily substances is dependent, inter alia, on whether compositions with a low viscosity (e.g. lotions)

are desired, or compositions with a high viscosity (e.g. creams, ointments).

Suitable organic solvents are preferably mono- and polyhydric alcohols, optionally ethoxylated polyethylene glycols, propylene glycol esters, sorbitol and derivatives thereof, glycol ether, propylene glycol ether and/or fatty esters.

The content of organic solvents can be up to 90% by weight, preferably 5 to 70% by weight.

Suitable cationic polymers are the compounds known under the INCI name "Polyquaternium", in particular polyquaternium-31, polyquaternium-16, polyquaternium-24, polyquaternium-7, polyquaternium-22, polyquaternium-39, polyquaternium-28, polyquaternium-2, polyquaternium-1 0, polyquaternium-1 1, and also polyquaternium-37&mineral oil&PPG trideceth (Salcare SC95), PVP-dimethylaminoethyl methacrylate copolymer, guar hydroxypropyltriammonium chlorides, and also calcium alginate and ammonium alginate. Also suitable are cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers (e.g. amidomethicones); copolymers of adipic acid and dimethylaminohydroxypropyldiethylenetriamine; polyaminopolyamides and cationic chitin derivatives (e.g. chitosan).

Examples of suitable silicone compounds are dimethylpolysiloxane, methylphenylpolysiloxanes, cyclic silicones and amino-, fatty acid-, alcohol-, polyether-, epoxy-, fluorine- and/or alkyl-modified silicone compounds, and also polyalkylsiloxanes, polyalkylarylsiloxanes and polyether siloxane copolymers, which may either be liquid or else resin-like at room temperature.

Depending on the intended use, suitable film formers are water-soluble polyurethanes (e.g. C10-polycarbamyl polyglyceryl ester), polyvinyl alcohol, polyvinylpyrrolidone, polyvinylpyrrolidone copolymers (e.g. vinylpyrrolidone/vinyl acetate copolymers), water-soluble acrylic acid polymers/copolymers and esters or salts thereof (e.g. partial ester copolymers of acrylic/methacrylic acid), polyethylene glycol ethers of fatty alcohols (e.g. acrylate/steareth-20 methacrylate copolymer), water-soluble cellulose (e.g. hydroxymethylcellulose, hydroxyethylcellulose, hydroxypropylcellulose), water-soluble quaterniums, polyquaterniums, carboxyvinyl polymers (e.g. carbomers and salts thereof) and/or polysaccharides (e.g. polydextrose, glucan).

Examples of suitable superfatting agents are polyethoxylated lanolin derivatives, lecithin derivatives, polyol fatty acid esters, monoglycerides and fatty acid alkanolamides, the latter also serving as foam stabilizers.

Available moisturizing substances are, for example, isopropyl palmitate, glycerol and/or sorbitol.

Stabilizers which can be used are metal salts of fatty acids, such as, for example, magnesium stearate, aluminum stearate and/or zinc stearate.

Biogenic active ingredients are to be understood as meaning, for example, plant extracts and vitamin complexes.

The compositions according to the invention can be mixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances as care additive.

Examples of suitable UV filters are 4-aminobenzoic acid; 3-(4'-trimethylammonium)benzylideneboran-2-one methylsulfate; 3,3,5-trimethylcyclohexyl salicylate; 2-hydroxy-4-methoxybenzophenone;
2-phenylbenzimidazole-5-sulfonic acid and its potassium, sodium and triethanolamine salts;
3,3'-(1,4-phenylenedimethine)bis(7,7-dimethyl-2-oxobicyclo[2.2.1]heptane-1-methanesulfonic acid and its salts;
1-(4-tert-butylphenyl)-3-(4-methoxyphenyl)propane-1,3-dione, 3-(4'-sulfo)benzylidenebornan-2-one and its salts;
2-ethylhexyl 2-cyano-3,3-diphenylacrylic acid;
polymer of N-[2(and 4)-(2-oxoborn-3-ylidenemethyl) benzyl]acrylamide;
2-ethylhexyl 4-methoxycinnamate;
ethoxylated ethyl 4-aminobenzoate;
isoamyl 4-methoxycinnamate; 2,4,6-tris[p-(2-ethylhexyloxycarbonyl)anilino]-1,3,5-triazine;
2-(2H-benzotriazol-2-yl)-4-methyl-6-(2-methyl-3-(1,3,3,3-tetramethyl-1-(trimethylsilyloxy)disiloxanyl)propyl) phenol;
bis(2-ethylhexyl) 4,4'-[(6-[4-((1,1-dimethylethyl) aminocarbonyl)phenylamino]-1,3,5-triazin-2,4-yl) diimino]bis(benzoate);
3-(4'-methylbenzylidene)-D,L-camphor;
3-benzylidenecamphor; 2-ethylhexyl salicylate;
2-ethylhexyl 4-dimethylaminobenzoate;
hydroxy-4-methoxybenzophenone-5-sulfonic acid (sulisobenzonum) and the sodium salt; and/or 4-isopropylbenzyl salicylate.

Examples of pigments/micropigments which can be used are microfine titanium dioxide, mica-titanium oxide, iron oxides, mica-iron oxide, zinc oxide, silicon oxides, ultramarine blue and chromium oxides.

Examples of suitable antioxidants are amino acids (e.g. glycine, histidine, tyrosine, tryptophan) and derivatives thereof, imidazoles (e.g. urocanic acid and derivatives thereof), peptides (e.g. D,L-carnosine, D-carnosine, L-carnosine and derivatives thereof, such as, for example, anserine), carotenoids, carotenes (e.g. α-carotene, β-carotene, lycopene and derivatives thereof), lipoic acid and derivatives thereof (e.g. dihydrolipoic acid, aurothioglucose, propylthiouracil), thiols (e.g. thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof, and also the salts thereof), dilauryl thiodipropionate, distearyl thiodipropionate, thiodipropionic acid and derivatives thereof (e.g. esters, ethers, peptides, lipids, nucleotides, nucleosides and salts) and/or sulfoximine compounds (e.g. buthionine sulfoximines), homocysteine sulfoximine, buthioninesulfones, penta-, hexa-, heptathionine sulfoximine, metal chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid, folic acid and derivatives thereof), ubiquinone and ubiquinol and derivatives thereof, vitamin C and derivatives thereof (e.g. ascorbyl palmitates, Mg ascorbyl phosphates, ascorbyl acetates), tocopherol and derivatives thereof (e.g. vitamin E acetate), vitamin A and derivatives thereof (e.g. vitamin A palmitate), coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc compounds (e.g. ZnO, ZnSO4), selenium compounds (e.g. selenomethionine), stilbenes and derivatives thereof (e.g. stilbene oxide, trans-stilbene oxide).

Oil-soluble compounds are advantageously used as antioxidants. The compositions comprise antioxidants, based on the finished compositions, preferably in amounts of from 0.001 to 30% by weight, particularly preferably 0.05 to 20% by weight, especially preferably 1 to 10% by weight.

Examples of suitable preservatives are phenoxyethanol, parabens, pentanediol or sorbic acid.

Dyes which can be used are the substances approved and suitable for cosmetic purposes.

Suitable fungicidal active ingredients are, preferably, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrethione and octopyrox.

Preferred acidic active ingredients are glycolic acid, lactic acid, citric acid, tartaric acid, mandelic acid, salicylic acid, ascorbic acid, pyruvic acid, oligooxa mono- and dicarboxylic acids, alpha-hydroxy acids, fumaric acid, retinoic acid, sulfonic acids, benzoic acid, kojic acid, fruit acid, malic acid, gluconic acid and/or derivatives of the above-mentioned compounds.

The compositions are preferably adjusted to a pH in the range 2 to 12, preferably 3 to 8.

The compositions are preferably emulsions of the oil-in-water or water-in-oil type.

The emulsions can be prepared in a manner known per se, i.e. for example by hot, hot/cold or PIT emulsification.

The emulsions are preferably day creams, night creams, care creams, nutrient creams, cleansing milk, skin milk, sunscreen lotion, skin protection creams, body lotions, ointments and the like.

Because of their good compatibility, the compositions according to the invention are particularly suitable as compositions for the cleansing, care or medicinal treatment of the skin, scalp, hair, nails or mucous membranes.

The compositions according to the invention are also suitable as vehicles for cosmetic and pharmaceutical active ingredients for the skin, the active ingredients preferably being antioxidants which protect the skin against oxidative stress.

The examples below serve to illustrate the invention in more detail without, however, limiting it thereto.

Preparation of the copolymers:

EXAMPLE 1

A 1000 ml flask fitted with anchor stirrer, reflux condenser, internal thermometer, inlet means for $N_2$ and $NH_3$ is charged with 490.5 g of tert-butanol and 11.5 g of water. 80.75 g of 2-acrylamido-2-methylpropanesulfonic acid were then introduced and dispersed with vigorous stirring, during which clouding of the solvent was retained. Over a period of 30 minutes, 6.64 g of ammonia are introduced into the gas headspace, and the mixture is stirred for at least a further 30 minutes until a pH of 6–7 is established. 4.10 g of N-vinylpyrrolidone and 0.8 g of allyl methacrylate are added thereto, and the receiver is rinsed each time with tert-butanol (about 6 ml) in order to minimize losses during the addition. The reaction mixture is then heated to a temperature of T=60° C., the reaction mixture being rendered inert by simultaneously introducing $N_2$. After a temperature of T=60° C. has been reached, 1.0 g of dilauryl peroxide is added. The reaction starts directly after the addition of the initiator, which is recognizable from an increase in the temperature and flocculation of the polymer. Approximately 15 minutes after the start of the polymerization reaction, the nitrogen feed is switched off. Approximately 30 minutes after the addition of the dilauryl peroxide, the temperature reaches a maximum (about 65–70° C.). A further 30 minutes after this maximum has been passed through, the mixture is heated to reflux and after-stirred for two hours under these conditions. The contents of the reaction vessel take on a pasty consistency over the course of the reaction, but are still readily stirrable. The mixture is then cooled to room temperature and the solid is filtered off with suction. The paste is dried at 60–70° C. over 24 hours in a vacuum drying cabinet, giving 92.2 g of a fine white powder.

EXAMPLE 2

Reaction procedure analogous to example 1, but using 1.65 g of trimethylolpropane methacrylate in place of allyl methacrylate.

EXAMPLE 3

Reaction procedure analogous to example 1, but using 35 g of 2-acrylamido-2-methylpropanesulfonic acid, 55 g of N-vinylpyrrolidone and 1.9 g of trimethylolpropane triacrylate as monomers.

EXAMPLE 4

Reaction procedure analogous to example 1, but using 77.5 g of 2-acrylamido-2-methylpropanesulfonic acid, 8.9 g of N-vinylpyrrolidone, 4.2 g of vinylformamide and 1.8 g of trimethylolpropane triacrylate as monomers.

Applications:

Acid stability of the copolymers:

Table 1 demonstrates the drastically higher acid stability of the copolymers compared with a ®Carbopol grade based on acrylic acid (Carbopol® 934 from Goodrich).

TABLE 1

| | Acid stability of the copolymers | |
|---|---|---|
| PH | Copolymer as in example 1 | ® Carbopol 934 |
| 6–7 | 65 600 mPa · s | 76 600 mPa · s |
| About 3 | 52 100 mPa · s | 140 mPa · s |

The acid stability was determined by measuring the viscosity at 25° C. with a Brookfield viscometer RVT model at 20 rpm. The viscosity determination was carried out on 1.0% strength gels (dissolution of the polymer powders in distilled water), the pH of which optionally being adjusted to an acidic pH (pH=about 3) and a neutral pH (pH=6-7) by adding NaOH or citric acid.

Storage stability of the compositions according to the invention:

Using the copolymers prepared in examples 1 to 4, the compositions 1 to 4 according to the invention were prepared in accordance with the formulation procedure given below. For comparison purposes, composition 5 comprising a ®Carbopol 980 was prepared.

Formulation procedure for the preparation of compositions 1 to 5 (all data in % by weight):

| | | |
|---|---|---|
| A | Almond oil | 7.00% |
| | ® Dow Corning 345 Cyclomethicone | 5.00% |
| B | Copolymers as in ex. 1 to 4 or ® Carbopol 980 | 1.00% |
| C | Water | ad 100% |
| | Glycerol | 8.00% |
| | Preservative (Nipa) | q.s. |
| D | Fragrance | 0.30% |

Preparation

I Mix A and B

II Mix the components of C

III Add II to I

IV Add D to I

V Homogenize emulsion, pH 4.5

The following stability tests are carried out:

a) Storage at 40° C., 45° C. and 50° C. over a period of 90 days.

b) Centrifugation at 20° C. for 30 minutes at 5000 rpm.

The results of the stability test for compositions 1 to 5 are summarized in table 2.

TABLE 2

Stability of compositions 1 to 5

| | Storage 40° C. | Storage 45° C. | Storage 50° C. | Centrifuge test |
|---|---|---|---|---|
| Composition 1 (copolymer ex. 1) | Stable | stable | stable | stable |
| Composition 2 (copolymer ex. 2) | Stable | stable | stable | stable |
| Composition 3 (copolymer ex. 3) | Stable | stable | unstable | stable |
| Composition 4 (copolymer ex. 4) | Stable | stable | stable | stable |
| Composition 5, comparison (® Carbopol 980) | Unstable | unstable | unstable | stable |

The compositions 1 to 4 according to the invention exhibit good emulsion stability during storage at 40° C., 45° C. and 50° C. over a period of 90 days and upon centrifugation (200 C., 30 minutes, 5000 rpm). The compositions according to the invention are also light and fresh and have moisturizing properties. The feel on the skin is pleasantly smooth and velvety.

The cream gel absorbs rapidly into the skin and is neither oily nor sticky.

The comparison formulation 5 containing ®Carbopol 980 is not storage-stable. The addition of 3% by weight of emulsifier ®Hostaphat KL 340 D, mono-, di- and tri(alkyl tetraglycol ether)-o-phosphoric acid esters, Clariant) gives an O/W emulsion which is stable in the storage test.

Application Examples 5 to 9:

EXAMPLE 5

Surfactant-free O/W Skin Milk with Keratolytic Action

| | | |
|---|---|---|
| A | Copolymer from example 1 | 2.00% |
| | Mineral oil | 4.00% |
| | Almond oil | 4.00% |
| | ® Cetiol SN (Henkel) Cetearyl isononanoate | 2.00% |
| C | Water | ad 100% |
| | Citric acid | 0.30% |
| | Malic acid | 0.40% |
| | Glycolic acid | 0.70% |
| | Lactic acid | 0.70% |
| D | Fragrances | 0.30% |

Preparation

I Mix the components of C and add to A

II Stir D into I

III Homogenize emulsion, pH 3.5

EXAMPLE 6

Surfactant-free Moisturizing Lotion

| | | |
|---|---|---|
| A | Almond oil | 7.00% |
| | Cyclomethicones | 5.00% |
| B | Copolymer from example 2 | 1.50% |
| C | Glycerol | 7.00% |
| | Water | ad 100% |
| | Preservative | q.s. |
| D | Fragrance | 0.30% |

Preparation

I Mix A and B

II Stir solution of C into I

III Add D to II

IV Homogenize

V pH 5.5

EXAMPLE 7

Surfactant-free Refreshing Lotion

| | | |
|---|---|---|
| A | Almond oil | 5.00% |
| | Cyclomethicone | 5.00% |
| B | Copolymer from example 4 | 1.50% |
| C | Glycerol | 3.00% |
| | Ethanol | 20.00% |
| | Water | ad 100% |
| | Preservative | q.s. |
| D | Fragrance | 0.30% |

Preparation

I Mix A and B

II Stir solution of C into I

III Add D to II

IV Homogenize

EXAMPLE 8

Surfactant-free Lotion with Refreshing, Invigorating Action

| A | Jojoba oil | 3.00% |
|---|---|---|
|   | Almond oil | 3.00% |
|   | Cetiol V | 3.00% |
|   | Decyl oleate |   |
| B | Copolymer from example 1 | 1.50% |
| C | Glycerol | 3.00% |
|   | Menthol | 0.70% |
|   | Camphor | 0.30% |
|   | Ethanol | 5.00% |
|   | Water | ad 100% |
|   | Preservative | q.s. |
| D | Fragrance | 0.30% |

Preparation

I Mix A and B

II Stir solution of C into I

III Add D to II

IV Homogenize

EXAMPLE 9

Surfactant-free Sunscreen Lotion

| A | Vaseline | 5.00% |
|---|---|---|
|   | Paraffin oil | 10.00% |
|   | Copolymer from example 1 | 0.75% |
|   | Tocopheryl acetate | 1.00% |
|   | Octyl methoxycinnamate | 2.00% |
|   | Parasol 1789 | 0.20% |
| B | Ethanol | 10.00% |
| C | Butylene glycol | 5.00% |
|   | Water | ad 100% |

Preparation

I Heat A and C separately to 75° C., then combine A and C and cool with stirring to 65° C., homogenize and cool further to 35° C.

II Stir B into I, homogenize and cool to room temperature.

We claim:

1. A surfactant-free cosmetic composition which comprises:

I) at least one copolymer consisting essentially of
a1) 1 to 50% by weight of the copolymer of the repeat structural unit of the formula (1)

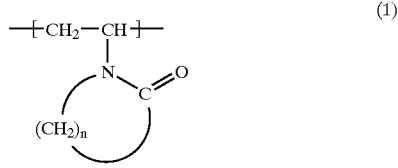
(1)

where n is an integer from 2 to 9, or a2) 1 to 50% by weight of the copolymer of a mixture of the repeat structural unit of the formula (1) and the repeat structural unit of the formula (2)

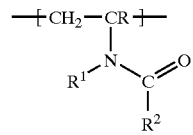
(2)

where R, $R^1$ and $R^2$ may be identical or different and are hydrogen or a linear or branched alkyl or alkenyl group having in each case 1 to 30 carbon atoms and b) 49.99 to 98.99% by weight of the copolymer of the repeat structural unit of the formula (3)

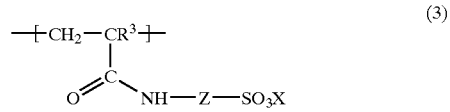
(3)

in which $R^3$ is hydrogen, methyl or ethyl, Z is $(C_1-C_8)$-alkylene, and X is an ammonium, alkali metal or alkaline earth metal ion and c) 0.01 to 8% by weight of crosslinking structures derived from the group consisting of allyl acrylate or methacrylate, trimethylolpropane triacrylate, trimethylolpropane trimethacrylate, dipropylene glycol diallyl ether, polyglycol diallyl ether, triethylene glycol divinyl ether, hydroquinone diallyl ether, tetraallyloxyethanes tetraethylene glycol diacrylate, triallylamine, trimethylolpropane diallyl ether, methylenebisacrylamide, divinylbenrene, and mixtures thereof II) 2 to 95% by weight of an oily substance; and III) water wherein said surfactant-free cosmetic composition comprises a stable composition.

2. The surfactant-free cosmetic composition of claim 1, wherein the copolymer consists of 2 to 30% by weight of the structural units a1) or a2), 69.5 to 97.5% by weight of the structural unit b) and 0.01 to 5% by weight of the crosslinking structures c).

3. The surfactant-free cosmetic composition of claim 1, wherein the copolymer consists of 3 to 15% by weight of the structural units a1) or a2), 84.5 to 96.5% by weight of the structural unit b) and 0.2 to 3% by weight of the crosslinking structures c).

4. The surfactant-free cosmetic composition of claim 1, wherein the copolymer consists of the structural unit a2).

5. The surfactant-free cosmetic composition of claim 1, wherein the structural unit according to formula (1) is derived from N-vinylpyrrolldone.

6. The surfactant-free cosmetic composition of claim 1, wherein X in the structural unit b) is $NH_4^+$.

7. The surfactant-free cosmetic composition of claim 1, wherein the crosslinking structures c) are derived from the group consisting of allyl acrylate, allyl methacrylate, trimethylolpropane triacrylate, trimethylolpropane trimethacrylate, and mixtures thereof.

8. The surfactant-free cosmetic composition of claim 1, which comprises 0.01 to 10% by weight of the copolymer, based on the weight of said composition.

9. The surfactant-free cosmetic composition of claim 1, which further comprises organic solvents, cationic polymers, silicone compounds, film formers, superfatting agents, moisturizing agents, biogenic active ingredients, glycerol, preservatives, pearlizing agents, dyes and fragrances, hydrotropic agents, opacifiers, thickeners, dispersants, collagen hydrolysates, polypeptides, egg yolk, lecithin, lanolin deodorizing agents, substances with a keratolytic and keratoplastic action, enzymes, carrier substances, antioxidants, UV light protection filters, pigments and metal oxides, agents with an antimicrobial action and/or acidic active ingredients.

10. The surfactant-free cosmetic composition of claim 1, which further comprises 5 to 70% by weight of organic solvents, based on the total weight of said composition.

11. The surfactant-free cosmetic composition of claim 1, which has a pH of from 2 to 12.

12. The surfactant-free cosmetic composition claim 1, which has a pH of less than 6.5.

13. The surfactant-free cosmetic composition of claim 1 which is an emulsion.

14. The surfactant-free cosmetic composition of claim 1 which is a cream selected from the group consisting of a night cream, care cream, nutrient cream, cleansing milk, skin milk, sunscreen lotion, skin protection cream, and a body lotion or ointment.

15. The surfactant-free cosmetic composition of claim 1, which is a dermatological composition.

16. The surfactant-free cosmetic composition of claim 1, which is a skin cosmetic composition.

17. The surfactant-free cosmetic composition of claim 1, which is a hair cosmetic composition.

18. The surfactant-free cosmetic composition of claim 1, which is a pharmaceutical composition.

19. The surfactant-free cosmetic composition of claim 1, which is a dermatological care composition.

20. The surfactant-free cosmetic composition of claim 1, wherein the oily substances are selected from the group consisting of silicone oils, phenylsilicones, silicone resins and gums, mineral oils, animal oil, vegetable oils, synthetic oils, linear and/or branched fatty alcohols and fatty acid esters, esters of linear ($C_6$–$C_{13}$)-fatty acids with linear ($C_6$–$C_{20}$)-fatty alcohols, esters of branch ($C_8$–$C_{13}$)-carboxylic acids with linear ($C_6$–$C_{20}$)-fatty alcohols, esters of linear ($C_8$–$C_{18}$)-fatty acids with branched alcohols, esters of linear and/or branched fatty acids with polyhydric alcohols and/or Guerbet alcohols, triglycerides based on ($C_6$–$C_{10}$)-fatty acids, esters, waxes optionally in combination with hydrophilic waxes, fluorinated and perfluorinated oils; fluorinated silicone oils, and mixtures thereof.

* * * * *